US005260488A

United States Patent [19]

Lim et al.

[11] Patent Number: 5,260,488

[45] Date of Patent: Nov. 9, 1993

[54] $N^1$-TRIFLUOROALKYL SUBSTITUTED 2-NITRO-P-PHENYLENEDIAMINE DYES

[75] Inventors: Mu-Ill Lim, Trumbull; Yuh-Guo Pan, Stamford, both of Conn.

[73] Assignee: Clairol Inc., New York, N.Y.

[21] Appl. No.: 852,278

[22] Filed: Mar. 16, 1992

Related U.S. Application Data

[62] Division of Ser. No. 759,282, Sep. 13, 1991, Pat. No. 5,186,716.

[51] Int. Cl.$^5$ ........ C07C 211/52
[52] U.S. Cl. ........ 564/441
[58] Field of Search ........ 564/441

[56] References Cited

U.S. PATENT DOCUMENTS

| | | | |
|---|---|---|---|
| 3,562,333 | 2/1971 | Schmidt-Collerus | 260/577 |
| 3,591,638 | 7/1971 | Halasz | 564/441 |
| 3,978,061 | 8/1976 | Kalopissis et al. | 260/570.5 |
| 4,419,101 | 12/1983 | Bugaut et al. | 564/367 |
| 4,666,453 | 5/1987 | Junino et al. | 564/441 |
| 4,981,486 | 1/1991 | Grollier et al. | 564/441 |

FOREIGN PATENT DOCUMENTS

| | | | |
|---|---|---|---|
| 1286738 | 8/1972 | United Kingdom | 564/441 |

OTHER PUBLICATIONS

J. Corbett, *J. Soc. Cosmet. Chem.*, 35, pp. 297–310 (1984).

*Primary Examiner*—Richard L. Raymond
*Attorney, Agent, or Firm*—Morton S. Simon

[57] ABSTRACT

$N^1$-Trifluoroalkyl substituted 2-nitro-p-phenylenediamines, compositions containing same, and their use as direct dyes for keratinous fibers are disclosed.

9 Claims, No Drawings

$N^1$-TRIFLUOROALKYL SUBSTITUTED 2-NITRO-P-PHENYLENEDIAMINE DYES

RELATED APPLICATION

This is a division of applications' co-pending application Ser. No. 07/759,282, filed Sep. 13, 1991, now U.S. Pat. No. 5,188,716.

FIELD OF INVENTION

The present invention relates to $N^1$-trifluoroalkyl substituted 2-nitro-p-phenylenediamines, compositions containing same, and their use in the dyeing of keratinous fibers.

DESCRIPTION OF THE RELATED ART 2-nitro-p-phenylenediamine and its derivatives have been used for many years in oxidative and direct dye compositions. This is because a wide range of colors is available simply by changing the substitution pattern on the amino nitrogens. Thus, a bright orange-red color is produced from the parent 2-nitro-p-phenylenediamine, while a violet blue color is produced from $N^1$, $N^4$, $N^4$-trisubstituted derivatives. Indeed, in the study of a wide range of such derivatives Corbett has shown that these color shifts are independent of the chemical nature of the substituent. For example, the N1 substituents, methyl and 2-hydroxyethyl, produce-an average bathochromic spectral shift of $26\pm2$ nm versus hydrogen for the series of 11 compounds studied. (J. Corbett, J. Soc. Cosmet. Chem. 35., 297–310, 1984: see Table IV.)

While this effect has accounted for the versatility and extreme usefulness of this series of compounds, it is also responsible for a serious drawback. As the following Table I shows even a single simple substituent changes the color from orange-red to magenta.

TABLE I

| Spectroscopic Data | | | | | | |
|---|---|---|---|---|---|---|
| | 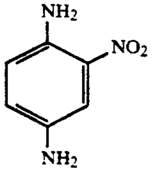 | 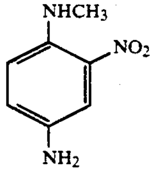 | 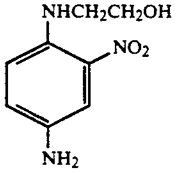 | 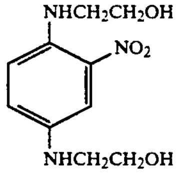 | 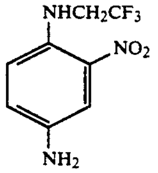 | 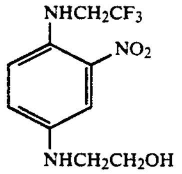 |
| | (II) | (III) | (IV) | (V) | (VI) | (VII) |
| 95% EtOH | | | | | | |
| $\lambda_{max}$ nm | 471 | 497 | 495 | 513 | 472 | 490 |
| | red | magenta | magenta | violet | red | magenta |

Consequently, only the single compound, 2-nitro-p-phenylenediamine, can produce the orange-red colors absolutely essential for the warm mahogany and coppery chestnut hair dyeing shades.

Unexpectedly we have found that the substituent, trifluoroethyl group, surprisingly has no effect on the spectral properties of the 2-nitro-p-phenylenediamine compounds (see Table I) and gives a color-identical to the unsubstituted analog. Thus, for the first time, the present invention makes it possible to color hair orange-red with a substituted 2-nitro-p-phenylenediamine. The trifluorcethyl substituent permits the dye chemist to manipulate solubility (hence shampoo-fastness) and light fading properties of the dye and thus aids the formulating chemist to produce more desirable hair coloring products than are currently available.

In addition, as Table I shows, this effect is also maintained when other substituents are present (compare IV, V and VII). Thus, important changes can be made in dye properties without consequent changes in color.

Although the N-trifluoroalkyl group is a known substituent in organic chemistry, (e.g. U.S. Pat. No. 3,562,333 discloses N-trifluoroalkyltrinitroanilines) the utility of this substituent in direct dyeing has not heretofore been appreciated.

None of the known direct hair dyes contains a $N^1$-trifluoroalkyl group. Moreover, none of the prior art references teaches or suggests the compounds of the present invention, compositions containing same, or their use as dyes for keratinous fibers.

SUMMARY OF THE INVENTION

Accordingly, one object of the present invention is to provide a compound of the formula I:

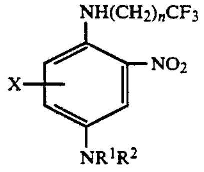

(I)

wherein:

n is 1 or 2;

$R^1$ and $R^2$ are each, independently, hydrogen, $C_{1-6}$ alkyl, $C_{1-6}$ hydroxyalkyl or $C_{1-6}$ (poly)hydroxyalkyl; and X is hydrogen, $C_{1-6}$ alkyl, $C_{1-6}$ alkoxy, or halogen.

Another object of the present invention is to provide compositions comprising an amount of a compound of formula I effective to dye a keratinous fiber.

Another object of the present invention is the use of compounds of formula I as dyes for keratinous fibers.

DETAILED DESCRIPTION OF THE INVENTION

Compounds of the formula I

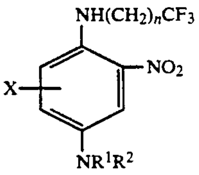

(I)

wherein:

n is 1 or 2;

$R^1$ and $R^2$ are each, independently, hydrogen, $C_{1-6}$ alkyl, $C_{1-6}$ hydroxyalkyl or $C_{1-6}$ (poly)hydroxyalkyl; and X is hydrogen, $C_{1-6}$ alkyl, $C_{1-6}$ alkoxy, or halogen; are useful as dyes for keratinous fibers. They are especially useful as direct hair dyes.

In the compounds of formula I:

"$-(CH_2)_n-$", wherein n is 1 or 2, encompasses methylene, and ethylene;

"$C_{1-6}$ alkyl" means an alkyl chain, straight or branched, containing 1 to 6 carbon atoms; examples are: methyl, ethyl, n-and iso-propyl, n-,sec-,and tert-butyl, hexyl, and the like;

"$C_{1-6}$ hydroxyalkyll" means an alkyl chain, straight or branched, containing 1 to 6 carbon atoms, and substituted by a hydroxyl group; examples are: hydroxymethyl, 2-hydroxyethyl, 3-hydroxy-n-propyl, and the like;

"$C_{1-6}$ (poly) hydroxyalkyll" means an alkyl chain, straight or branched, containing 1 to 6 carbon atoms, and substituted by 1 to 3hydroxyl groups; examples are: 1,2-dihydroxyethyl, 2,3-hydroxypropyl, 4,3,2,-trihydroxy-n-butyl, and the like;

"$C_{1-6}$ alkoxyl" means an alkyl chain, straight or branched, containing 1 to 6 carbon atoms, and linked to the phenyl ring through an oxygen atom; examples are: methoxy, ethoxy, n-propoxy, n-,iso-and tert butoxy, hexoxy, and the like; and "halogen" means chlorine, bromine, fluorine, and iodine.

Preferred compounds of the present invention are those wherein n is equal to 1; the preferred $N^1$-substituent being 2,2,2-trifluoroethyl.

Other preferred compounds are:

those wherein $R^1$ and $R^2$ are each independently: hydrogen, $C_{1-3}$ alkyl, or $C_{1-3}$ hydroxyalkyl;

those wherein X is hydrogen, $C_{1-3}$ alkyl, $C_{1-3}$ alkoxy, chlorine, or bromine;

those wherein at least one of $R^1$ and $R^2$ is hydrogen;

those wherein $R^1$ is hydrogen and $R^2$ is $C_{1-3}$ hydroxyalkyl; and those wherein X is hydrogen.

More preferred compounds of formula 1 are:

$N^1$-(2,2,2,-trifluoroethyl)-$N^4$-(2,3-dihydroxypropyl)-2-nitro-p-phenylenediamine;

$N^1$-(2,2,2,-trifluoroethyl)-$N^4$-bis(2-hydroxyethyl)-2-nitro-p-phenylenediamine;

$N^1$-(2 2 2, -trifluoroethyl)-$N^4$-(2-hydroxyethyl)-$N^4$-methyl-2-nitro-p-phenylenediamine; and $N^1$(2,2,2,-trifluoroethyl)-$N^4$-(2,3-dihydroxypropyl)-$N^4$-methyl-2-nitro-p-phenylenediamine.

Most preferred compounds of formula I are:

$N^1$-(2,2,2,-trifluoroethyl)-2-nitro-p-phenylenediamine and $N^1$-(2,2,2,-trifluoroethyl)-$N^4$-(2-hydroxyethyl)-2-nitro-p-phenylenediamine.

Another object of the present invention is the provision of a composition for dyeing a keratinous fiber, said composition comprising:

a) an amount sufficient to dye said fiber, of a compound of the formula I:

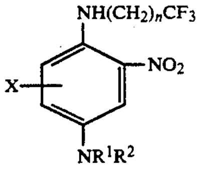

(I)

wherein:

n is 1 or 2;

$R^1$ and $R^2$ are each, independently, hydrogen, $C_{1-6}$ alkyl, $C_{1-6}$ hydroxyalkyl, or $C_{1-6}$ polyhydroxyalkyl; and X is hydrogen, $C_{1-6}$ alkyl, $C_{1-6}$ alkoxy, or halogen; and b) a cosmetically acceptable carrier.

Preferred compositions are:

those containing the compound of formula I, wherein n is 1; those containing the compound of formula 1, wherein $R^1$ and $R^2$ are each, independently, hydrogen, $C_{1-3}$ alkyl, or $C_{1-3}$ hydroxyalkyl;

those containing the compound of formula I, wherein, X is hydrogen, $C_{1-3}$ alkyl, $C_{1-3}$ alkoxy, chlorine, or bromine; those containing the compound of formula I, wherein, at least one of $R^1$ and $R^2$ is hydrogen; and those containing the compound of formula I, wherein, $R^1$ is hydrogen and $R^2$ is $C_{1-3}$ hydroxyalkyl.

More preferred compositions are those wherein the compound of formula I is:

$N^1$-(2,2,2,-trifluoroethyl)-$N^4$-(2,3-dihydroxypropyl)-$N^4$-methyl-2-nitro-p-phenylenediamine;

$N^1$-(2,2,2-trifluoroethyl)-$N^4$-bis(2-hydroxy-ethyl)-2-nitro-p-phenylenediamine;

$N^1$-(2,2,2-trifluoroethyl)-$N^4$-(2-hydroxyethyl)-$N^4$-methyl-2-nitro-p-phenylenediamine; and $N^1$-(2,2,2-trifluoroethyl)-$N^4$-(2,3-dihydroxypropyl)-$N^4$-methyl-2-nitro-p-phenylenediamine.

Most preferred compositions are those wherein the compound of formula I is: $N^1$-(2,2,2-trifluoroethyl)-2-nitro-p-phenylene-diamine or $N^1$-(2,2,2-trifluoroethyl)-$N^4$-(2-hydroxy-ethyl)-2-nitro-p-phenylenediamine.

The pH of the above composition may vary from about 3 to about 11.

The concentration of the compound of formula I to be employed in the dye composition may vary somewhat depending on the nature of the carrier, the presence of other hair dyes, the results desired, and the like. All that is required is that an effective amount of the compound of formula I be employed. Generally, however, the compound of formula I is present in the composition in an amount of from about 0.01% to about 10%, preferably from about 0.1% to about 5%, by weight, based on the total weight of the dye composition.

As used herein, the term "dye composition" means the total composition, including the compound(s) of formula I, other dye(s) (if present), carrier(s) and adjuvant(s).

The cosmetically acceptable carriers employed in the dye compositions of the present invention may vary in complexity from simple solutions, aqueous dispersions, or hydroalcoholic dispersions, to very complex systems, such as thickened shampoos.

Water will ordinarily constitute the major component of the dye compositions of this invention. The amount of water employed can vary widely depending on the types and quantity of adjuvants or additives contained in the composition. Water may constitute as little as 10% by weight of the dye composition, based on the total weight of the composition. Generally, it constitutes from about 70% to about 90% by weight, based on the total weight of the composition.

It is often advantageous to include in the dye compositions of the present invention, an organic solvent or solvent system which helps solubilize the dyes and adjuvants contained therein. A number of organic solvents are known in the art that are useful for such purpose. These include alcohols (particularly alkyl alcohols of 1-6 carbons, especially ethanol and propanol); glycols of up to about 10 carbons (especially diethylene glycol monobutyl ether) carbitols; and benzyl alcohol. When present, the organic solvents will, based on the total weight of the dye composition, constitute from about 1% to about 60%, preferably from about 10% to about 30%, of the dye composition.

The dye compositions of this invention may also contain other conventional adjuvants or additives commonly found in direct hair dye compositions. For example, they may include, surface active agents, thickening agents, alkalizing agents, chelating agents, perfumes, and the like.

The surface active agents are typically water soluble (less preferably, they may he water dispersible). The surface active agents may be anionic, nonionic or cationic surface active agents. Illustrative of the various types of water soluble surface active agents which can be employed are: higher alkyl benzene sulfonates; alkyl naphthalene sulfonates; sulfonated esters of alcohols and poly acids; taurates; fatty alcohol sulfates; sulfates of branched chain or secondary alcohols; alkyl dimethylbenzyl ammonium chlorides, and the like.

Examples of surfactants that may be utilized are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethylbenzylammonium chloride; dodecylbenzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate, and the like. The quantity of water soluble surface active agent employed can vary widely; however it is usually employed in an amount of up to about 15%, preferably from about 0.10% to about 10%, based on the total weight of the composition.

The thickening agent, when employed, may be one or several of those commonly used in hair dyeing; for example, sodium alginate; gum arabic; cellulose derivatives (such as methylcellulose and sodium carboxymethylcellulose), acrylic polymers (such as polyacrylic acid sodium salt), and inorganic thickeners (such as bentonite). The quantity of thickening agent employed can vary over a wide range. Typically it is employed in an amount of up to about 20%, preferably from about 0.1% to about 5%, based on the total weight of the composition.

The compositions of the present invention can also contain conventional oxidation dyes, e.g., p-phenylenediamine, α-naphthol, p-aminophenol, m-aminophenol, resorcinol and m-phenylenediamine, and their derivatives, which in the presence of a conventional oxidizer such as hydrogen peroxide provide a range of shades on the hair. Similarly, the dyes herein disclosed can be used in combination with other conventional semipermanent dyes, e.g., o- and p-nitroanilines, nitro-p-phenylenediamines, aminoanthraquinones, aminoazobenzenes, and- their derivatives.

A third object of the present invention is to provide a process for dyeing a keratinous fiber. The process comprises contacting the keratinous fiber with an amount of a dye composition sufficient to dye the fiber, said composition comprising:

a) a compound of the formula I:

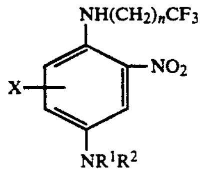

(I)

wherein:

n is 1 or 2;

$R^1$ and $R^2$ are each, independently, hydrogen, $C_{1-6}$ alkyl, $C_{1-6}$ hydroxyalkyl, or $C_{1-6}$ polyhydroxyalkyl; and X is hydrogen, $C_{1-6}$ alkyl, $C_{1-6}$ alkoxy, or halogen; and b) a cosmetically acceptable carrier.

Preferred processes are those whereins in the formula I, n is 1.

Other preferred processes are those wherein, in the formula I $R^1$ and $R^2$ are each, independently, hydrogen, $C_{1-3}$ alkyl, or $C_{1-3}$ hydroxyalkyl.

Other preferred processes are those which employ the compound of formula I, wherein X is hydrogen, $C_{1-3}$ alkyl, $C_{1-3}$ alkoxy, chlorine, or bromine;

those which employ the compound of formula I in which at least one of $R^1$ and $R^2$ is hydrogen;

those which employ the compound of formula I, in which X is hydrogen; and those which employ the compound of formula U in which $R^1$ is hydrogen and $R^2$ is $C_{1-3}$ hydroxyalkyl.

More preferred processes are those which employ as the compound of formula I:

$N^1$-(2,2,2-trifluoroethyl)-$N^4$-(2,3 dihydroxypropyl)-2-nitro-p-phenylenediamine;

$N^1$-(2,2,2-trifluoroethyl)-$N^4$-bis (2-hydroxyethyl)-2-nitro-p-phenylenediamine;

$N^1$-(2,2,2-trifluoroethyl)-$N^4$-(2hydroxy-ethyl)-$N^4$-methyl-2-nitro-p-phenylenediamine; and $N^1$-(2,2,2-trifluoroethyl)-$N^4$-(2,3-dihydroxypropyl)-$N^4$-methyl-2-nitro-p-phenylenediamine.

Most preferred processes are those employing the compound of formula I, $N^1$-(2,2,2 -trifluoroethyl)-2 -nitro-p-phenylenediamine or $N^1$-(2,2,2-trifluoroethyl)-$N^4$-(2-hydroxyethyl)2-nitro-p-phenylenediamine.

The present inventors have surprisingly found that $N^1$-(2,2,2-trifluoroethyl)-2-nitro-p-phenylenediamine, a compound of the instance invention, has an absorption maximum in the red region and imparts red coloration to hair. The color obtained is almost identical to that of 2-nitro-p-phenylenediamine despite the fact that the two compounds have different molecular size and molecular weight (153 vs 235). UV/Visible spectra of the compounds also show the spectroscopic similarity. 2-Nitro-p-phenylenediamine has $\lambda_{max}$ at 471 nm in 95% ethanol while $N^1$-(2,2,2-trifluoroethyl) -2-nitro-p-phenylenediamine absorbs at 472 nm. This is surprising because all other known $N^1$-alkylsubstituted 2-nitro-p-phenylenediamines have a $\lambda_{max}$ around 495 nm and dye hair magenta. (see J. F. Corbett, J. Soc. Cosmet. Chem., 35, 297-818, 1984).

The present inventors have also surprisingly found that $N^1$-(2,2,2-trifluoroethyl)-$N^4$-(2-hydroxyethyl)-2-nitro-p-phenylenediamine, another compound of the instant invention, absorbs at 490 nm and dyes hair magenta. This is surprising since all other known $N^1$, $N^4$-disubstituted-2-nitro-p-phenylenediamines show a $\lambda_{max}$ around 513 nm and impart a violet color to the hair.

The dye composition of the present invention can be applied to living human hair on the head by conventional techniques well-known in the art. For example, it can be poured over the hair or applied with a brush, sponge, or other means of contact, until the hair is properly impregnated. The time of contact of the dye composition with the hair is not critical. It can vary over the wide range typically used in the hair dyeing art. For example, periods of about 5 minutes to 2 hours or more, preferably from about 10 to 60 minutes, can be employed. The dyeing of live hair is preferably carried out at a temperature below 40° C. More preferably, it is carried out at a temperature of about 15° C. to about 40° C. Most preferably, it is carried out at ambient room temperature, e.g. about 20° C. to about 35° C.

The compounds of formula I may be prepared according to the reaction path shown in the following illustrative Scheme 1, or by any other conventional method known in the art.

using trifluoroethylamine in dimethylsulfoxide. Treatment of 6 with 2-chloroethylchloroformate and calcium carbonate in dioxane produces 8. Compound 8 in the presence of potassium hydroxide in ethanol and water yields 9.

Compounds 1 to 9 can be substituted by halogen, alkoxy and/or alkyl. Starting compound 1 may be prepared according to methods well-known in the art.

The dye compositions of this invention can be prepared by conventional methods used in the hair dyeing art. Thus, they can be prepared by dissolving or dispersing the dye in water to produce a desired concentration. Water miscible organic solvents can be employed to facilitate solution of the dye. The dye can first be dissolved in the solvent and then diluted with water. Dispersion of the various ingredients can be facilitated by heating the composition.

The following examples are merely offered to illustrate the present invention. They are not intended to limit its scope.

EXAMPLE 1

(a) Preparation of N-(2,2,2-trifluoroethyl)-2-nitroaniline (4)

A mixture of o-fluoronitrobenzene (1) (7. 05 g, 50 mmol), 2,2,2-trifluoroethylamine (14.85 g, 3 eq.) and DMSO (20 ml) was heated at 120° C. in an autoclave for 24 hrs., then poured onto crushed ice/$H_2O$. The resultant yellow-orange precipitate was collected by filtration, washed with $H_2O$ three times and air-dried to give 10.58 g (98% yield) of N-(2,2,2-trifluoroethyl)-2-nitroaniline (4): mp 84°-89° C.; MS m/e 220(m+); $^1H$ NMR (DMSO-$d_6$)δ4.38 (m, 2H), 6.84 (t, 1H, J=7.6 Hz), 7.32 (d, 1H, J=8.7 Hz), 7.62 (t, 1H, J=7.8 Hz) 8.12 (d, 1H, J=8.7 Hz), 8.31 (1H, —NH).

Scheme 1:

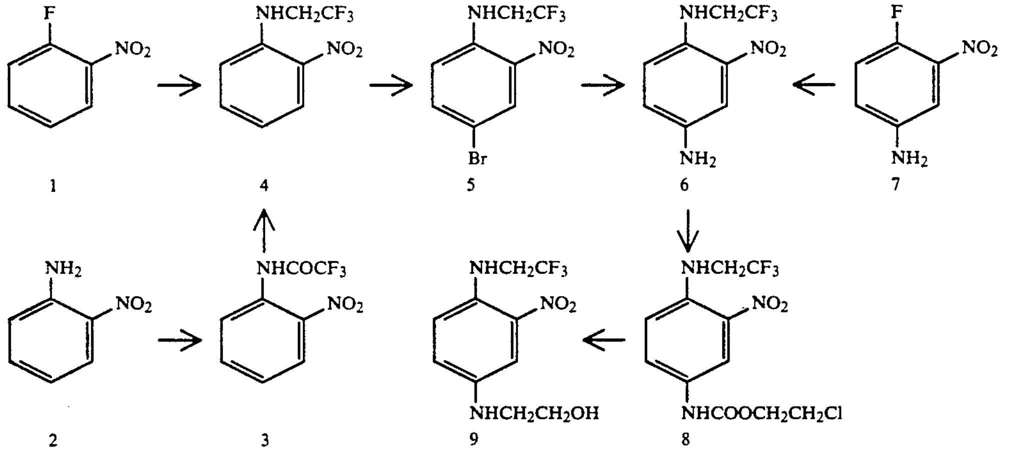

1 4 5 6 7

2 3 9 8

The starting material, o-fluoranitrobenzene 1, is commercially available. Nucleophilic substitution of 1 with 2,2,2-trifluoroethylamine, in dimethylsulfoxide, at 120° C. for 24 hrs., affords 4. Compound 4 can also be prepared from o-nitroaniline 2 using trifluoroacetic anhydride in ether to give 3. Treatment of 3 with $NaBH_4$ and $ZnBr_2$, in dioxane, produces 4. Selective bromination of 4 with bromine, in acetic acid and at room temperature, affords 5. Amination of 5 with concentrated ammonium hydroxide in the presence of cuprous iodide (or cupric oxide, capper, or cuprous acetate) yields 6. Compound 6 can also be prepared from 4-fluoro-3-nitroaniline 7

(b) Preparation of N-(2,2,2-trifluoroethyl)-4-bromo-2-nitro aniline (5)

Bromine (2.33 ml, 2 eq.) in acetic acid (15 ml) was added dropwise to a stirred solution of N-(2,2,2-trifluoro- ethyl)-2-nitroaniline (4) (5.0g, 23 mmol) in acetic acid (50 ml), in an ice bath. After the bromine addition was completed, the i-ce bath was removed and the -reaction mixture was stirred at room temperature for 30 minutes and poured onto crushed ice. The resultant yellow-orange precipitate was collected by filtration, washed with $H_2O$ three times and air dried to give 6.0 g (88% yield) of N-(2,2,2,-trifluoroethyl)-4-bromo-2-nitroaniline (5): mp 118°-120° C.; MS m/e 298 (M+), $^1$HNMR (DMSO-$d_6$) δ4.33 (m, 2H), 7.28 (d, 1H, J=9.0 Hz), 7.72 (dd, 1H, J=2.2 Hz, 9.0 Hz), 8.18 (d, 1H, J=2.1 Hz), 8.31 (1H, -NH).

(c) Preparation of $N^1$-(2,2,2-trifluoroethyl)-2-nitro-p-phenylenediamine (6)

A mixture of 5 (8.0g, 27 mmol), $NH_4OH$ (50 ml) and CuI (0.80 g) was heated at 120° C. in an autoclave for 28 hours. The mixture was poured into $H_2O$, extracted with ethylacetate and the organic layer was washed with brine and water three times, dried ($Na_2SO_4$) and evaporated to give 4.0 g (63% yield) of 6 as a red solid. The compound was purified by silica gel column (40/60 ethylacetate/hexane) : mp 104°-106° C., MS m/e 235 (M+) $^1$HNMR (DMSO-$d_6$)δ4.38 (m,2H) 5.07 (s,2H,$NH_2$), 7.03 (dd,1H, J=2.4 Hz, 9.0 Hz), 7.11 (d,1H, J=9.3 Hz), 7.30 (s,IH, J=2.4 Hz), 7.86 (1H,NH).

(d) Preparation of $N^1$-(2,2,2-trifluoroethyl)-$N^4$-(2-hydroxy ethyl)-2-nitro-p-phenylenediamine (9)

A mixture of $N^1$-(2,2,2,-trifluoroethyl)-2-nitro-p-phenylene-diamine (6) (0.705 g, 3 mmol), 2-chloroethyl chloroformate (0.515 g, 3.6 mmol) and $CaCo_3$ (0.40 g, 4 mmol) in dioxane (10 ml) was stirred at 80° C. for 20 minutes, filtered and washed with ethyl acetate. The combined filtrate was washed with water and brine, dried (Na2SO4), and evaporated to give a brown oil. Trituration with hexane gave 2-chloroethyl-N-[4-(2,2,2-trifluoroethyl)-3-nitrophenyl]-carbamate (8) as an orange solid. The unpurified carbamate (8) was dissolved in aqueous ethanol (ETOH: $H_2O$, 15/5 ml) and powdered KOH (1.35 g) was added. The mixture was stirred at 90° C. for 20 minutes and then poured onto crushed ice (20 g) . The resultant mixture was extracted with ethyl acetate, washed with water and brine, dried ($Na_2SO_4$), and evaporated to give 0.544 g (65% yield) of $N^1$-(2,2,2-trifluoroethyl)-$N^4$-(2-hydroxyethyl)-2-nitro-p-phenylenediamine (9): mp 93°-95° C.; MS m/e 279(M+); $^1$HNMR (acetone-$d_6$), δ3.25 (m, 2H), 3.76 (m, 2H), 3.91 (bs, 1H), 4.34 (m, 2H), 4.98 (bs, 1H), 7.19 (m, 2H), 7.35 (s,1H), 7.80 (bs, 1H).

EXAMPLES 2-4

The following compositions were used to color hair:

| | Examples | | |
|---|---|---|---|
| | 2* | 3* | 4* |
| $N^1$-(2,2,2-trifluoroethyl) 2-nitro-p-phenylenediamine (6) | 0.15 g | 1.0 g | — |
| $N^1$-(2,2,2-trifluoroethyl)-$N^4$-2-hydroxyethy)-2-nitro -p-phenylenediamine (9) | — | — | 0.04 g |
| Ethanol (95%) | 10.00 g | 5.00 g | — |
| Isopropanol | — | — | 5.00 |
| Hydroxyethyl cellulose | — | 0.50 g | — |
| Trithanolamin | — | 1.50 g | — |
| Water | 10.00 g | 92.00 g | 15.00 g |
| | 20.15 g | 100.00 g | 20.04 g |

*:pH adjusted to 9.5 with MEA.

The compositions of Examples 2, 3 and 4 were used to dye swatches of blended gray hair in accordance with the following procedure:

The hair was soaked in the dye solution at room temperature for 30 minutes and then rinsed with water. The compositions of Examples 2 and 3 were found to dye hair red. The composition of Example 4 dyed hair magenta.

The dyed hair was subjected to a series of six shampoos and water rinses to determine washfastness. Washfastness results in all three cases were good.

We claim:

1. A compound of the formula:

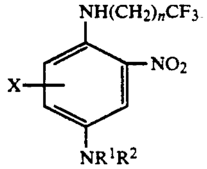

(I)

wherein:

n is 1 or 2;

$R^1$ and $R^2$ are each, independently, hydrogen, $C_{1-6}$ alkyl, $C_{1-6}$ hydroxyalkyl or $C_{1-6}$ (poly)hydroxyalkyl; and X is hydrogen, $C_{1-6}$ alkyl, $C_{1-6}$ alkoxy, or halogen.

2. The compound of claim 1, wherein n is 1.

3. The compound of claim 2, wherein $R^1$ and $R^2$ are each, independently, hydrogen, $C_{1-3}$ alkyl, or $C_{1-3}$ hydroxyalkyl.

4. The compound of claim 3, wherein X is hydrogen, $C_{1-3}$ alkyl, $C_{1-3}$ alkoxy, chlorine, or bromine.

5. The compound of claim 4, wherein at least one of $R^1$ and $R^2$ is hydrogen.

6. The compound of claim 5, wherein X is hydrogen.

7. The compound of claim 6, wherein $R^1$ is hydrogen and $R^2$ is $C_{1-3}$ hydroxyalkyl.

8. The compound of claim 1, being $N^1$-(2,2,2-trifluoroethyl)-$N^4$-(2-hydroxyethyl)-2-nitro-p-phenylenediamine.

9. The compound of claim 1, being $N^1$-(2,2,2-trifluorethyl)-2-nitro-p-phenylenediamine.

* * * * *